(12) United States Patent
Rodgers et al.

(10) Patent No.: US 7,232,550 B1
(45) Date of Patent: Jun. 19, 2007

(54) COMBINATION ROOM FRESHENER AND OIL CANDLE AND METHOD FOR MAKING THE SAME

(75) Inventors: Ronald W. Rodgers, Lynchburg, VA (US); Steven L. Fullerton, Forest, VA (US); Jennifer M. Smith, Lynchburg, VA (US)

(73) Assignee: TRI Tech Laboratories, Inc., Lynchburg, VA (US)

( * ) Notice: Subject to any disclaimer, the term of this patent is extended or adjusted under 35 U.S.C. 154(b) by 487 days.

(21) Appl. No.: 10/243,725

(22) Filed: Sep. 16, 2002

(51) Int. Cl.
*A61L 9/03* (2006.01)

(52) U.S. Cl. ............ 422/125; 422/126; 431/126; 431/289; 431/290; 431/321

(58) Field of Classification Search ............ 422/5, 422/125, 126; 44/275, 519, 600; 431/126, 431/289, 291, 320, 321
See application file for complete search history.

(56) References Cited

U.S. PATENT DOCUMENTS

| 275,293 | A |   | 4/1883 | Tisdale |
| D111,775 | S |   | 10/1938 | Seaver |
| D150,000 | S |   | 6/1948 | Cohen |
| 3,898,039 | A |   | 8/1975 | Lin |
| 3,958,917 | A |   | 5/1976 | Naz |
| 4,025,280 | A | * | 5/1977 | Wilson ............ 431/1 |
| 4,427,366 | A |   | 1/1984 | Moore |
| 4,892,711 | A |   | 1/1990 | Tendick, Sr. |
| 4,931,014 | A |   | 6/1990 | Scott et al. |
| 5,395,233 | A |   | 3/1995 | Karp |
| 5,840,257 | A | * | 11/1998 | Bureau et al. ............ 422/125 |
| D411,891 | S |   | 7/1999 | Bell et al. |
| D414,656 | S |   | 10/1999 | Richmond |
| 6,033,210 | A |   | 3/2000 | Freeman |
| D424,219 | S |   | 5/2000 | Toscano et al. |
| 6,210,153 | B1 |   | 4/2001 | Freeman et al. |
| 6,214,063 | B1 |   | 4/2001 | DeStefano et al. |
| 6,241,512 | B1 |   | 6/2001 | Freeman et al. |
| 6,333,009 | B1 | * | 12/2001 | Allison ............ 422/125 |
| 6,371,453 | B1 | * | 4/2002 | Hunter ............ 261/107 |
| 6,667,006 | B2 | * | 12/2003 | Richards ............ 422/4 |

FOREIGN PATENT DOCUMENTS

WO   WO03007999 A1  *  1/2003

* cited by examiner

*Primary Examiner*—E. Leigh McKane
(74) *Attorney, Agent, or Firm*—Sughrue Mion, PLLC

(57) ABSTRACT

A fluid-burning lamp that delivers a fragrance(s) and is aesthetically pleasing. The fluid-burning lamp includes a fragrance-dispensing element that contains a material that slowly melts and forms a liquid pool when the lamp is lit. The slow-melting material gives the fluid-burning lamp the appearance of a traditional wax candle, when the lamp is viewed from the top. Other elements of the fluid-burning lamp include a fluid container for holding a combustible fluid to be used as fuel for the burn, and a wick assembly containing a wick having a lower portion that extends into the combustible fluid. The fluid container for holding the combustible fluid may also hold various immersions, such as, for example, fruits, colored marbles, leaves, seeds, sprigs, or flowers, in order to provide the ultimate in flexibility for home décor.

14 Claims, 3 Drawing Sheets

US 7,232,550 B1

COMBINATION ROOM FRESHENER AND OIL CANDLE AND METHOD FOR MAKING THE SAME

BACKGROUND OF THE INVENTION

The invention relates to a device for dispensing a fragrance(s) into the atmosphere and, in particular, to a fragrance-dispensing, fluid-burning lamp, and a method of making the same.

There is a growing demand for light-providing home décor items that can both decorate and scent a home. Thus, the model of the ideal home décor item is being transformed from a strictly utilitarian product to a fashionable hybrid that not only brightens a space, but also aesthetically enhances the space and provides it with a welcome fragrance.

Gel compositions and candles are a pair of home décor items currently being used to extend, via fragrance, a room's décor or theme into an additional sensory dimension, or to evoke a particular feeling, mood, or season. These products, however, deliver a fragrance by actually burning a fragrance-containing gel or wax as fuel. They also tend to provide limited home décor value to the consumer.

Fluid-burning lamps are a popular home décor item that use a myriad of colors and, more recently, immersions to aesthetically enhance a space. The colors and immersions, however, tend to be included with the fuel source, promoting inefficiency in the combustion process and/or resulting in the production of excessive smoke and soot. The immersions, moreover, may be flammable and, thus, a safety concern if not properly isolated from the heat source. Still further, fluid-burning lamps do not possess the added advantage of delivering a fragrance.

U.S. Pat. No. 3,898,039 to Lin discloses an article comprising a substrate, a particulate carrier and a binder, at least part of at least one surface of the substrate bearing a fumigant, wherein the fumigant is diffusible from the article upon exposure to the thermal energy of a candle. Thus, the fragrant mixture of Lin is coated on the walls of the substrate, i.e., the candle container. The candle itself is a wax, such as paraffin wax or carnauba wax.

U.S. Pat. No. 3,958,917 to Naz discloses an odorizer for a candle. The odorizer is formed from a wax-like material impregnated by an odoriferous composition. The odorizer is adapted to overlay the lighted end of the candle and includes an opening permitting the wick of the candle to extend therethrough. The odorizer is consumed by the burning wick and paraffin of the candle.

U.S. Pat. No. 4,892,711 to Tendick, Sr. discloses a fragrance-dispensing device, including an annular element made from a solid, synthetic polymeric, plastic material, such as a low density polyethylene, containing from about 5 wt % to about 20 wt % of a vaporizable fragrance material uniformly dispersed throughout. When the wick is lit, heat from the burner vaporizes and drives the fragrance material from the plastic material. The appearance of the combination of the annular element and fragrance material therein does not change as the combination is heated. In other words, the device of the '711 patent does not mimic the appearance of a conventional candle.

In short, there exists a need for a fragrance-dispensing, fluid-burning lamp that (i) effectively delivers a fragrance (s), (ii) provides the aesthetic appeal of a fluid-burning lamp while avoiding the hazards commonly associated therewith, and (iii) appears as though it is burning like a traditional wax candle or gel composition when viewed from above.

SUMMARY OF THE INVENTION

There is provided a fluid-burning lamp that delivers a fragrance(s) and is aesthetically pleasing. The fluid-burning lamp comprises a fragrance dispensing-element that comprises a material that slowly melts and forms a liquid pool when the lamp is lit. The slow-melting material gives the fluid-burning lamp the appearance of a traditional wax candle or gel composition when the lamp is viewed from the top.

Other elements of the fluid-burning lamp include a fluid container for holding a combustible fluid to be used as fuel for the burn, and a wick assembly comprising a wick having a lower portion that extends into the combustible fluid.

The fluid container for holding the combustible fluid may preferably hold one or more immersions, such as, for example, fruits, colored marbles, leaves, seeds, sprigs, flowers, or glitter, in order to provide the ultimate in flexibility for home décor.

DETAILED DESCRIPTION OF THE INVENTION

Figure 1:
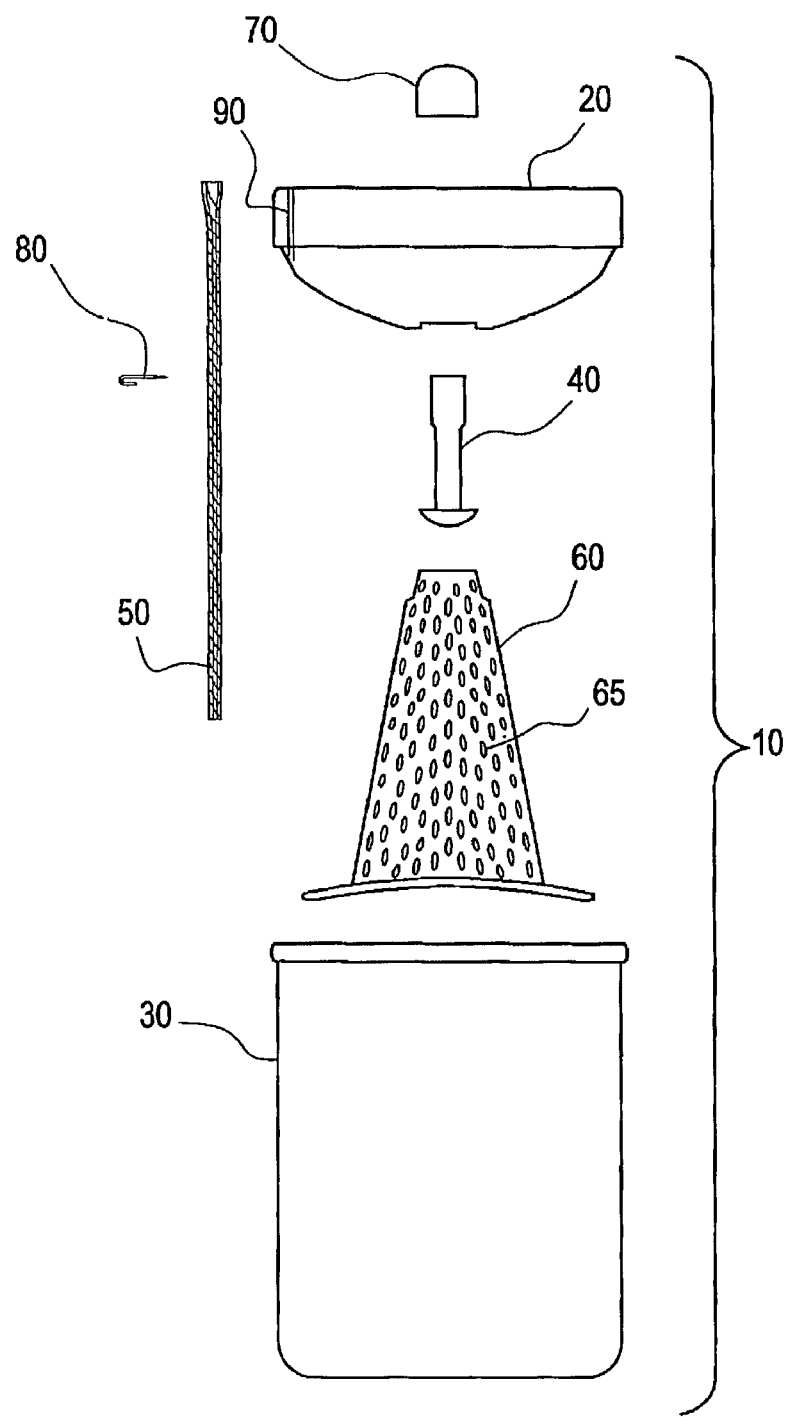
FIG. 1 is an exploded view of the lamp illustrated in FIG. 2.

The fluid-burning lamp comprises a fragrance-dispensing element.

The fragrance-dispensing element comprises a first container or receptacle for holding a material that slowly melts and forms a liquid pool when the lamp is lit, i.e., the slow-melting material. Preferably, the first container or receptacle is bowl-shaped, thereby exposing the slow-melting material contained therein to the environment. The first container or receptacle may be made of any suitable heat-resistant material, such as, for example, glass, ceramic, or acrylic. In a preferred embodiment, the first container or receptacle is glass.

The first container or receptacle may be described as having inner and outer surfaces, wherein at least a part of the inner surface is in contact with the slow-melting material and no part of the outer surface is in contact with the slow-melting material. The first container or receptacle has a first channel or hole through its center through which a wick threaded through a wick insert may be passed. The first channel or hole intersects both the inner and outer surfaces of the first container or receptacle.

As will be readily understood, the first container or receptacle has a thickness dimension as measured in a direction perpendicular to its inner and outer surfaces. For example, the first container or receptacle may be from 0.125 inch to 0.25 inch thick.

In an embodiment of the present invention, the first container or receptacle has a second channel or venting hole through its thickness dimension, e.g., a second channel or hole that passes through the thickness dimension and intersects the outer surface of the first container or receptacle at two locations, but does not intersect the inner surface of the first container or receptacle. The second channel or venting hole provides a vent to the atmosphere for a combustible fluid contained in a second container of the present fluid-burning lamp, when the first container or receptacle has been secured to the second container. Preferably, the second channel or venting hole has a narrow diameter, and is positioned in a particular manner, such that the combustible fluid of the second container cannot escape to the atmosphere through the second channel or venting hole, at least during the normal operation and movement of the present fluid-burning lamp. FIGS. 1–4, including second channel or venting hole 90, illustrate this embodiment of the invention.

The fragrance-dispensing element further comprises the slow-melting material. The slow-melting material has a high flash point and comprises, as a matrix, one or more different types of hydrocarbons. For example, an exemplary slow-melting material may have a flash point exceeding 340° F. (171° C.), e.g., from 360° F. to 385° F. (from 182° C. to 196° C.), and may include white mineral oil, in addition to other types of hydrocarbons. In a particular embodiment, the slow-melting material is a clear, odorless, soft gel having a flash point of 380° F. (193° C.) and comprising 85–95 wt % of white mineral oil, 5–10 wt % of gellant(s), and 0.01–0.1 wt % of butylated hydroxy toluene. In each case herein, the flash point is calculated in accordance with ASTM D-92.

One or more vaporizable perfume or fragrance additives are evenly dispersed throughout the hydrocarbon matrix, as a part of the slow-melting material. Preferably, a hydrocarbon matrix is selected with properties that allow for a high load of vaporizable perfume or fragrance additives. In addition, one or more pigments, dyes, or immersions, e.g., glitter, may be evenly dispersed throughout the hydrocarbon matrix to color or highlight the slow-melting material, and thereby enhance the decorative flexibility.

The slow-melting material should have a softening point low enough to allow some melting to occur upon exposure to heat when the lamp's wick is lit. For example, the slow-melting material may have a softening point less than the temperature produced by heat generated by the flame. The amount of heat generated by a flame, and the temperature the heat produces, varies depending on many factors, including the type of combustible fluid being used, but generally the amount of heat generated produces a temperature in the order of from about 100° F. to about 200° F. (from about 38° C. to about 93° C.), or even higher. The overall softening point of the slow-melting material decreases with increasing amounts of perfume or fragrance additives.

In general, a slow-melting material should be chosen with an appropriate softening point so that the areas of the slow-melting material closest to the radiant heat of the flame and wick assembly may slowly melt and form a liquid pool. In a particular embodiment, the slow-melting material has a softening point of 170° F. (77° C.) prior to the addition of any additives. Versagel CHP "A", available from Pennrico, and SYLVACLEAR PA20, a polyamide resin blend available from Arizona Chemical, are examples of slow-melting materials suitable for use in the present fluid-burning lamp.

The one or more vaporizable perfume or fragrance additives used must be capable of (i) being incorporated into and uniformly dispersed throughout the hydrocarbon matrix, and (ii) being vaporized at a temperature produced by the flame and wick assembly. Specifically, when the lamp's wick is lit, heat from the flame and wick assembly creates a liquid pool in the slow-melting material, including the perfume or fragrance additives, from which the additives are vaporized and driven into the surrounding environment. Various natural and synthetic oils, perfumes, and other conventional fragrance materials that are known to have these properties and to produce a desired odor, such as, for example, a floral odor, e.g., rose, a fruit odor, e.g., strawberry, or an odor of an edible, e.g., cinnamon, can be used as the additives. In one embodiment, the perfume or fragrance additives will be a mixture of several ingredients.

The amount of vaporizable perfume or fragrance additives used should be sufficient for the fragrance-dispensing element to continue releasing a noticeable fragrance throughout the life of the fluid-burning lamp, i.e., until the combustible fluid has been completely consumed. In one embodiment of the present invention, the amount of vaporizable perfume or fragrance additives included within the hydrocarbon matrix of the slow-melting material is greater than 20 wt %, e.g., up to about 45 wt %, based upon the total weight of the slow-melting material. Alternatively, the amount of vaporizable perfume or fragrance additives may be from about 5 wt % to about 20 wt %. Preferably, the burn rate of the combustible fluid and the longevity of the fragrance delivery are both set to from about 30 to about 40 hours.

The fluid-burning lamp comprises a second container, i.e., the fluid container, for holding the combustible fluid to be used as fuel for the burn. The second container may be made of any suitable heat-resistant material, such as, for example, glass, ceramic, or acrylic. In a preferred embodiment, the second container is glass. Although the first container or receptacle may be secured to the second container by various suitable means, in particular embodiments, the first container or receptacle is sealed to the top of the second container using a glass adhesive, including any of the glass adhesives of the art.

In one embodiment, the second container is in the shape of a cylinder, and has an open-ended top and a closed-ended bottom. The diameter of the cylindrical second container may be equal to the diameter of the first container or receptacle, e.g., the bowl-shaped first container or receptacle, at least at the point where the first container or receptacle and second container meet. The first container or receptacle is then tightly sealed to the open end of the second container with a glass adhesive, such that the slow-melting material contained in the first container or receptacle is exposed to the environment. In preferred embodiments, the second container contains a level of combustible fluid that reaches no less than ⅛ inch below the bottom of the first container and no more than ¼ inch below the bottom of the first container. Preferably, the level of combustible fluid is kept short of both the bottom of the first container and the bottom of a wick stand of the present fluid-burning lamp.

By virtue of the tight seal formed, the combustible fluid contained within the second container is unable to escape at the points where the first and second container meet. By virtue of the narrow diameter and positioning of the second channel or venting hole through the thickness of the first container (in those embodiments of the present invention comprising a second channel or venting hole), the combustible fluid contained within the second container is also unable to escape through the second channel or venting hole, at least during the normal operation and movement of the present fluid-burning lamp.

The combustible fluid to be used as fuel for the burn may be any lamp oil, such as, for example, a highly-refined paraffin-based lamp oil. The lamp oil may be transparent, or colored to provide greater decorative flexibility. It must be noted that the present invention delivers a fragrance by heating and vaporizing the perfume or fragrance additives of the slow-melting material; the slow-melting material is not being used as the fuel. The combustible fluid contained in the second container is the fuel.

In a preferred embodiment, the second container will also hold one or more types of immersions, such as, for example, glitter, fruits, colored marbles, leaves, seeds, sprigs, or flowers. The immersions may be natural or synthetic. In a particular embodiment, the immersions may be silk. The immersions further enhance the home décor flexibility of the fluid-burning lamp.

The fluid-burning lamp comprises a wick assembly. The wick assembly comprises a wick, a wick insert, and a wick stand.

Any type of wick may be used with the present fluid-burning lamp. In a preferred embodiment, the wick is nylon.

The wick is threaded through a wick insert. The wick insert may be, for example, cylindrical and made of glass. In a preferred embodiment, the wick insert is a tapered glass cylinder, e.g., the wick insert is approximately cone-shaped with a top side of the cylinder having a larger diameter than a bottom side of the cylinder. An example of this type of wick insert is shown as reference numeral 40 in FIGS. 1–4. A particular advantage of this type of wick insert is that a central portion of the wick insert has a comparatively narrow diameter that encompasses the threaded wick relatively tight. The wick is threaded through the wick insert so that a portion of the wick protrudes from each side of the wick insert. For example, the wick is threaded through the wick insert so that from about 0.125 inches to about 0.25 inches of the wick protrudes from the top side of the wick insert, and from about 4.5 inches to about 5.5 inches of the wick protrudes from the bottom side of the wick insert.

In certain embodiments, it may be important to permanently set the length of wick that protrudes from the top side of the wick insert, i.e., to permanently set the length of that portion of the wick that will be lit. The length of wick that is available to be lit is a factor in determining the amount of heat generated by the flame, and the amount of heat generated by the flame directly impacts the formation of the liquid pool in the slow-melting material. Accordingly, in certain embodiments, the wick and wick insert are adapted with means for preventing an end user of the fluid-burning lamp from pulling the wick further out from the wick insert, or pushing the wick further into the wick insert.

For example, the wick may be restrained from being pulled further out from the wick insert by setting the wick with a staple or pin. In particular, a staple or pin employed, e.g., just below the bottom of the wick insert can prevent an end user from pulling out the wick. FIGS. 1–4, including pin 80, illustrate this embodiment of the invention.

Alternatively, the wick may be permanently set by employing a material that collapses upon itself if an opposing force (in only one specific direction) is applied to its surface. The collapsible material would not be accessible to the end user. For example, the wick may be fed through the collapsible material during manufacture in the direction that does not allow collapse. A collapsible material located directly below the wick insert would cause an interference with the inner diameter of the wick insert in the event that the end user attempted to pull the wick out. The interference would serve to anchor the material, which in turn would allow the wick to cause the force that collapses the material in on itself.

Still another alternative for restraining the wick involves providing the inner wall of the wick insert with sharp points, or "fingers," protruding therefrom. The fingers may be aligned so as to allow the wick to pass through during manufacture. Thereafter, the fingers would impede wick movement if, for example, an end user attempted to push the wick down into the wick assembly.

Besides providing a stand for the wick, the wick stand serves as a channel for the wick and wick insert. Before the second container, i.e., the combustible fluid container, is filled with the combustible fluid and, if there are to be any, the immersions, and before the first container is sealed to the top of the second container, the wick stand is placed inside the second container to provide a stand, or channel, for the wick and wick insert.

The base of the wick stand is compatible with the bottom of the second container in order to provide a stable stand. For example, if the bottom of the second container is crowned, then the bottom of the wick stand is correspondingly crowned. A crowned wick stand 60 is illustrated in FIGS. 1–4.

The wick stand may be made of glass or a plastic, such as, for example, a polyvinyl chloride (PVC). The wick stand is made porous. For example, the wick stand may be a plastic that has been provided with pores, or holes, during the process of manufacturing the plastic, e.g., during an injection molding process. Preferably, the wick stand is cone-shaped, with the bottom of the cone having a larger diameter than the top of the cone.

Once the wick stand has been placed inside the second container, the combustible fluid and the immersions, if any immersions are being used, may also be placed inside the second container. The combustible fluid and immersions are added such that the wick stand creates a void space with respect to the immersions, but not with respect to the combustible fluid. The combustible fluid passes through the pores of the wick stand, but the immersions are kept outside of the space defined by the wick stand. Accordingly, the pores in the plastic wick stand are of a particular size and number so as to allow a maximum flow of combustible fluid to pass, while still keeping the immersions outside of the space defined by the wick stand.

As mentioned earlier, the first container or receptacle preferably has a hole in its center through which the wick insert may be passed. According to a preferred embodiment, the wick insert, with the wick threaded therethrough, is passed through the hole in the first container or receptacle.

The wick insert and first container or receptacle may be arranged such that when the wick insert is passed through the hole, the bottom of the wick insert is flush with the bottom of the first container or receptacle. Alternatively, the wick insert and first container or receptacle may be arranged such that a length of from about 0.25 inches to about 0.50 inches of the wick insert protrudes beyond the bottom of the first container or receptacle and into the second container.

In either case, a tight seal is formed between the first container or receptacle and the wick insert, such that the first container or receptacle may be sealed to the top of the second container using, e.g., a glass adhesive, and the combustible fluid in the second container is unable to escape at the point where the wick insert contacts the first container. The tight seal between the wick insert and the first container or receptacle may be formed in any suitable manner. For example, the bottom of the wick insert may be provided with a hemisphere, as illustrated by the wick insert 40 in FIGS. 1–4. The hemisphere has a flat top that may be used as a gluing surface for a suitable adhesive, including any of the glass or plastic adhesives known in the art. The hemisphere has a hole in order for the wick to pass through into the combustible fluid of the second container.

As already mentioned, the wick itself protrudes a certain length from the bottom of the wick insert. Accordingly, once the wick insert has been sealed to the first container or receptacle, and the first container or receptacle has been sealed to the second container, the wick is able to draw combustible fluid up from the second container to feed the flame.

In a preferred embodiment, the fluid-burning lamp is manufactured to be ready-to-use without any further assembly required by the end user. Specifically, the end user obtains the fluid-burning lamp with (i) the wick insert already passed through the first container or receptacle, (ii) the wick threaded through the insert and immersed in the combustible fluid, and (iii) the wick insert sealed in a manner that prevents seepage of the combustible fluid up through the wick insert and into the slow-melting material, or out of the lamp in general. The end user only has to remove the seal(s), and light the wick.

Therefore, in preferred embodiments, the fluid-burning lamp further comprises a liquid-tight lid, cap, or seal over the top of the wick and wick insert. Although the combustible fluid of the second container cannot escape through the second channel or venting hole during the normal operation and movement of the fluid-burning lamp, the second channel or venting hole (for those embodiments that contain a second channel or venting hole) may be liquid-tight sealed with, e.g., a pressure-sensitive sticker. Advantageously, it is not necessary to provide a lid, cap, or seal over the entire open end of the first container or receptacle, when the top of the wick insert and second channel or venting hole (if present) are liquid-tight sealed.

The lid, cap, or seal may be, for example, plastic, acrylic, ceramic, rubber or glass. Lid 70 illustrated in FIGS. 1–4 is one example of a lid that may be employed with the present fluid-burning lamp.

Figure 2:
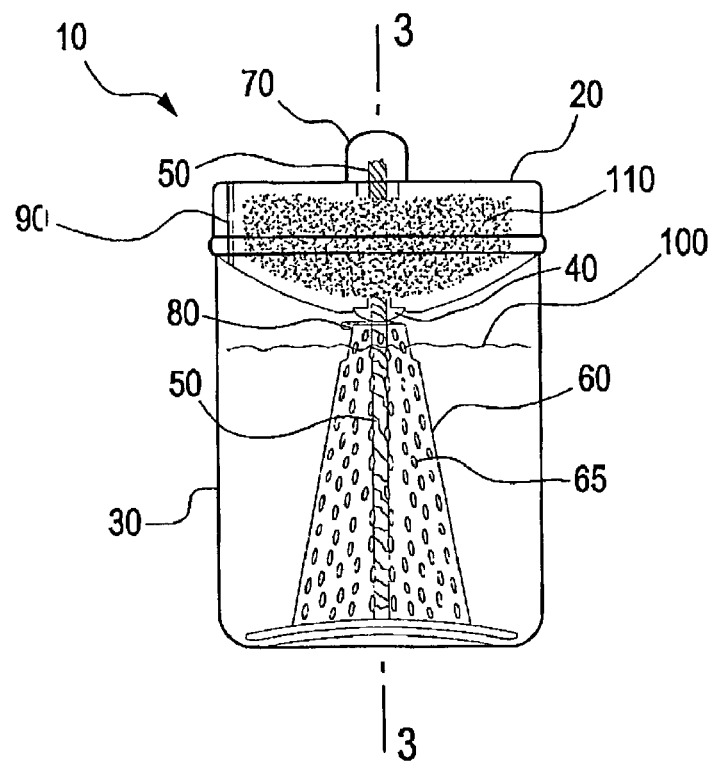
FIG. 2 is a plain view of a fluid-burning lamp according to one embodiment of the invention.
Figure 3:
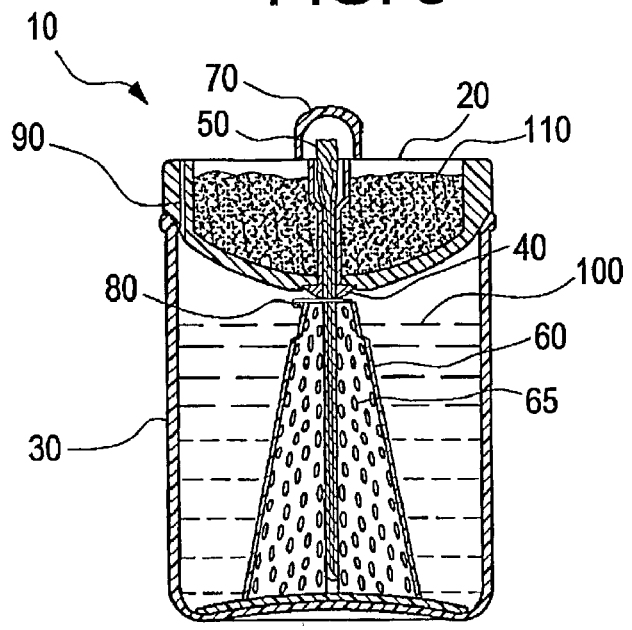
FIG. 3 is a section view of the lamp illustrated in FIG. 2.
Figure 4:
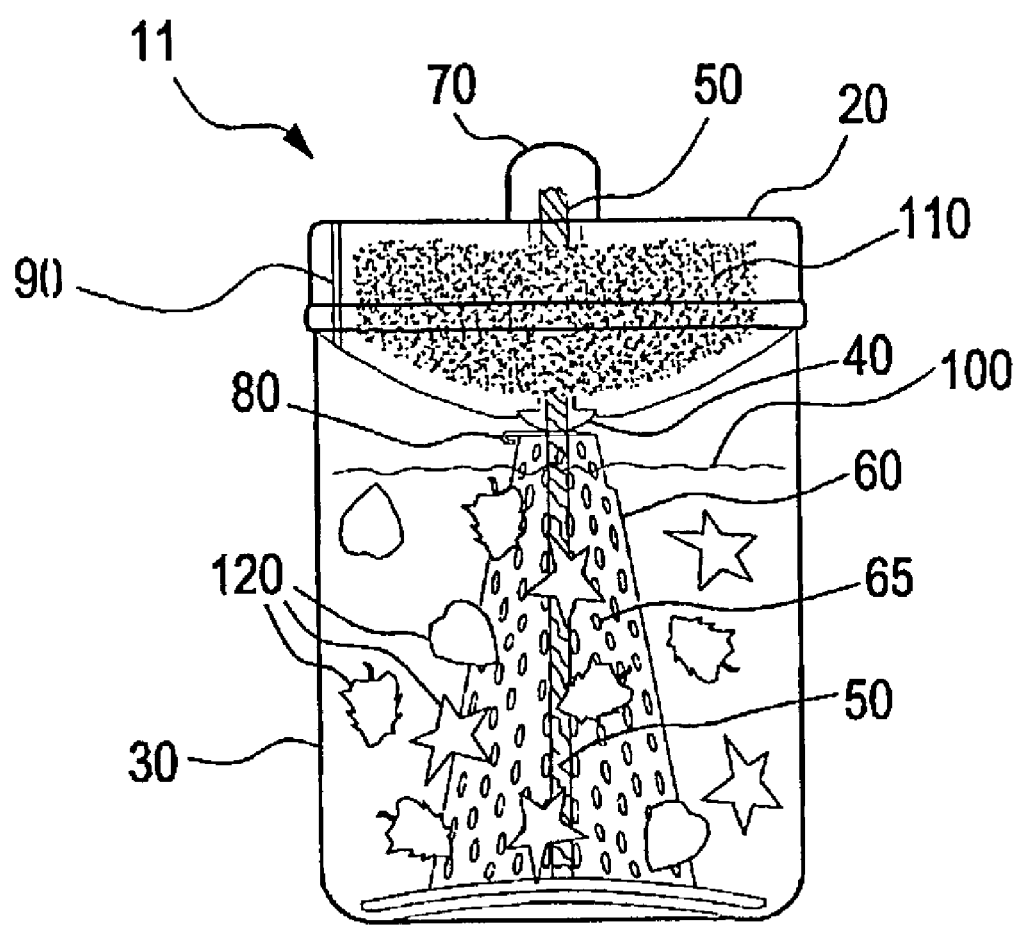
FIG. 4 is a plain view of a fluid-burning lamp according to another embodiment of the invention.

Illustrated in FIGS. 1, 2, 3, is a fluid-burning lamp 10 according to the present invention. Illustrated in FIG. 4 is a fluid-burning lamp 11 according to a particular embodiment of the present invention.

FIG. 1 presents an exploded view of a lamp 10, including a first container 20 for holding the slow-melting material, a second container 30 for holding the combustible fluid to be used as fuel for the burn, a wick insert 40, a wick 50, a wick stand 60 with pores 65, which not only provides a stand for the wick 50, but also serves as a channel for the wick 50, a lid 70 for the wick insert 40, and a pin 80 to prevent the wick 50 from being pulled out of the wick insert 40 by, e.g., an end user. A second channel or venting hole 90 passes through a thickness dimension of first container 20.

FIG. 2 is a plain view of lamp 10 comprising a transparent first container 20, a transparent second container 30, a transparent wick insert 40, a transparent wick stand 60 with pores 65, a transparent lid 70, a second channel or venting hole 90, clear, combustible fluid 100, and slow-melting material 110.

FIG. 3 is a section view of lamp 10. FIG. 3 clearly illustrates wick insert 40, with wick 50 threaded therethrough, passing through first container 20, such that the bottom of wick insert 40 protrudes just below the bottom of first container 20. Slow-melting material 110 is disposed inside first container 20 and around wick insert 40. Combustible fluid 100 and wick stand 60 with pores 65 are disposed inside second container 30. First container 20 is sealed onto second container 30 such that wick 50, which protrudes from the bottom of wick insert 40, is channeled through wick stand 60 and reaches near the bottom of second container 30. A pin 80 is disposed just below the bottom of wick insert 40 and prevents the wick 50 from being pulled out by an end user. A lid 70 forms a tight seal over the top of the wick 50 and wick insert 40. Thickness dimensions to first container 20, second container 30, wick stand 60, and lid 70 are clearly illustrated as well. The second channel or venting hole 90 passes through the thickness dimension of first container 20, intersecting an outer surface of first container 20 at two locations, but not intersecting an inner surface of first container 20.

FIG. 4 is a plain view of a lamp 11 identical to lamp 10, except that immersions 120 are provided in transparent second container 30 with clear, combustible fluid 100, such that transparent wick stand 60 creates a void space with respect to immersions 120, but not with respect to clear, combustible fluid 100. Clear, combustible fluid 100 passes through pores 65 of transparent wick stand 60, but immersions 120 are kept away from wick 50 by transparent wick stand 60.

From the foregoing description, one skilled in the art can easily ascertain the essential characteristics of the invention, and, without departing from the spirit and scope thereof, make various changes or modifications to adapt it to various usages.

What is claimed is:

1. A fluid-burning lamp, comprising:
   a wick;
   a first container comprising disposed therein a slow-melting material; and
   a second container comprising disposed therein a combustible fluid;
   wherein the slow-melting material comprises a hydrocarbon matrix having one or more vaporizable perfume or fragrance additives dispersed therein, the slow-melting material has a softening point less than the temperature produced by heat generated by a flame of the lamp, and the combustible fluid is contacted by the wick and provides fuel therefore,
   wherein the first container is sealed to the second container with an adhesive,
   wherein the fluid-burning lamp further comprises a wick insert having the wick threaded therethrough and a wick stand disposed in the second container for channeling the wick,
   wherein the second container further comprises one or more immersions selected from the group consisting of fruits, colored marbles, leaves, seeds, sprigs, flowers, and mixtures thereof, and
   wherein the wick stand is made of porous plastic, and the immersion are separated from the wick by the wick stand.

2. The fluid-burning lamp of claim 1, wherein the first container comprises a channel or venting hole for venting the combustible fluid of the second container.

3. The fluid-burning lamp of claim 1, wherein the wick is threaded through the wick insert such that a portion of the wick protrudes from each end of the wick insert.

4. The fluid-burning lamp of claim 3, wherein:
   a length of from about 0.125 inches to about 0.250 inches of the wick protrudes from a top opening of the wick insert;
   a length or from about 4.5 inches to about 5.5 inches of the wick protrudes from a bottom opening of the wick insert; and
   the top opening of the wick insert has a wider diameter than a central portion of the wick insert.

5. The fluid-burning lamp of claim 3, wherein the portion of the wick protruding from the bottom portion of the wick insert is immersed in the combustible fluid.

6. The fluid-burning lamp of claim 1, wherein the first container, second container and wick insert are each glass.

7. The fluid-burning lamp of claim 1, wherein the first container, second container and wick insert are each plastic.

8. The fluid-burning lamp of claim 1, wherein the wick insert is sealed to the first container with an adhesive.

9. The fluid-burning lamp of claim 1, further comprising means for preventing the wick from being pulled out or pushed through a top opening of the wick insert.

10. The fluid-burning lamp of claim 9, wherein the means for preventing the wick from being pulled out through a top opening of the wick insert comprises a pin or staple disposed below the wick insert.

11. The fluid-burning lamp of claim 1, further comprising a lid, seal, or cap disposed over a top opening of the wick insert having the wick threaded therethrough.

12. The fluid-burning lamp of claim 1, wherein the first container is a bowl-shaped glass and the second container is a cylinder having an open-ended top and a closed-ended bottom.

13. A fluid-burning lamp, comprising:
   a wick;
   a first container comprising disposed therein a slow-melting material;
   a second container comprising disposed therein a combustible fluid; and
   a wick stand, which is disposed only in the second container and has the wick channeled therethrough,
   wherein the slow-melting material comprises a hydrocarbon matrix having one or more vaporizable perfume or fragrance additives dispersed therein, the slow-melting material has a softening point less than the temperature produced by heat generated by a flame of the lamp, and the combustible fluid is contacted by the wick and provides fuel therefore, and
   wherein the wick stand is made of porous plastic, the second container further comprises one or more immersions selected from the group consisting of fruits, colored marbles, leaves, seeds, sprigs, flowers, and mixtures thereof, and the immersions are separated from the wick by the wick stand.

14. The fluid-burning lamp of claim 13, wherein the wick stand is a crowned wick stand.

* * * * *